ically equivalent exothermic reaction,
until cellulose in the lignocellulose is exhausted.

United States Patent [19]
Thrash et al.

[11] Patent Number: 4,573,447
[45] Date of Patent: Mar. 4, 1986

[54] CHEMICAL HEATER

[75] Inventors: Tommy K. Thrash, Littlefield; Richard W. Tock; Lyle V. Cox, both of Lubbock; W. Gregg Quattlebaum, Slaton, all of Tex.

[73] Assignee: Sunbelt America Corporation, Littlefield, Tex.

[21] Appl. No.: 703,685

[22] Filed: Feb. 19, 1985

[51] Int. Cl.$^4$ .............................................. F24J 1/02
[52] U.S. Cl. ..................................... 126/263; 44/3 A; 44/3 R; 128/403; 252/70
[58] Field of Search ............... 126/263; 44/3 R, 3 A, 44/3 B, 3 C; 252/70; 128/403

[56] References Cited

U.S. PATENT DOCUMENTS 4,067,313  1/1978  Donnely .............................. 126/263
4,282,005  8/1981  Sato et al. ............................ 44/3 R

FOREIGN PATENT DOCUMENTS 58-120699  7/1983  Japan ................................. 44/3 R Primary Examiner—Samuel Scott
Assistant Examiner—Allen J. Flanigan
Attorney, Agent, or Firm—Montgomery W. Smith; Wendell Coffee

[57]   ABSTRACT

A chemical heater combines cellulosic material and a hypochlorite salt in the presence of water for exothermic reaction. Although sodium hypochlorite may be used, calcium hypochlorite is the preferred hypochlorite salt as a reactant. The preferred cellulosic material is particles of cotton plants, in particular lint fibers recovered from gin trash, or non-lint, lignocellulose particles. The lignocellulose particles are preferably soaked with water prior to addition of the hypochlorite salt. Each subsequent addition of similar amounts of the hypochlorite salt to the soaked lignocellulose particles results in a substantially equivalent exothermic reaction, until cellulose in the lignocellulose is exhausted.

11 Claims, 6 Drawing Figures

CHEMICAL HEATER

CROSS REFERENCE TO RELATED APPLICATIONS

None. However, applicants filed Disclosure Document No. 128,782 on July 2, 1984 and Disclosure Document No. 131,111 on Sept. 24, 1984, which documents concern this application. Therefore, it is respectfully requested by separate paper that the document be retained and acknowledgement thereof made by the Examiner.

BACKGROUND OF THE INVENTION (1) Field of the Invention

This invention relates to chemical heaters.

(2) Description of the Prior Art

Prior to filing this application, a search was made in the public search files of the U.S. Patent and Trademark Office. That search developed the following references:

Reed eT aL: U.S. Pat. No. 3,233,604
Hollinshead: U.S. Pat. No. 3,585,982
Donnelly: U.S. Pat. No. 3,903,011
Krupa: U.S. Pat. No. 3,980,070
Donnelly: U.S. Pat. No. 4,067,313
Yoshida eT aL: U.S. Pat. No. 4,093,424
Kaiho eT aL: U.S. Pat. No. 4,199,548
Fujiwara: U.S. Pat. No. 4,205,957
Marshall eT aL: U.S. Pat. No. 4,265,216
Abe: U.S. Pat. No. 4,366,804

All of the above references disclose selected materials that produce heat by exothermic reaction when mixed. Yoshida eT aL and Kaiho eT aL disclose exothermic reactants or metal sulfides, poly sulfides, or hydrosulfides mixed with a catalyst carried by carbonaceous materials that react when exposed to air as an oxygen source. These two references also use a filler, such as waste of foamed synthetic resins, silica powder, wood dust or material, or synthetic fibers (e.g. polyester fibers, polystyrene and polyurethane foams, and cotton linters), that act as a heat buffer and heat sink. The filler disclosed does not take part in the reaction.

Fujiwara, Abe, Reed eT aL, and Krupa, disclose iron filings, or other metal particles, which are combined with an alkali metal salt, such as potassium chlorate, magnesium chloride, potassium nitrates, magnesium nitrates, among others, in aqueous solution, in some disclosures, in the presence of a catalyst, such as noble metals carried by carbonaceous materials. Abe also discloses a water carrying member to soak up water that is then fed to the dry reactants as needed. The water carrying member may include rubber, synthetic resin, cellulose, or other highly absorbent, nonreactive material.

Hollinshead discloses encapsulation of a reactant in a solution, with the capsules broken to mix exothermic reactants. The reactants disclosed by Hollinshead include, among others, peroxide, perborate and persulfate salts, reacted with magnesium, zinc, iron, aluminum sulfites, and barbituric acids.

Donnelly, in '011 and '313, discloses adding water to an anhydrous mixture of (a) calcium chloride, or other "primer," such as cerous chloride, cesium hydroxide, sodium carbonate, among other, and (B) an organic oxide or salt, such as calcium oxide, aluminum chloride, calcium nitrate.

Marshall eT aL disclose mixing magnesium chloride and ethylene glycol.

A few of the above cited references disclose various rupturable containers of one reactant or water or aqueous solution within a larger, impervious container also containing reactants. Marshall eT aL also disclose tear strips between separate compartments, whereas Hollinshead shows encapsulation to separate reactants. Other references simply provide for additions of water directly by the user.

SUMMARY OF THE INVENTION (1) New Function and Unexpected Results

We have invented a chemical heater that may be used as a personal body warmer, such as a stadium seat or hand warmer, or for warming cans, packages, or other articles. Our invention uses commonly available reactants, some of which were previously disposed of as trash, to produce the unexpected and surprising result of a convenient chemical heater when these reactants are combined.

Our invention reacts hypochlorite salts in the presence of water with cellulosic, or cellulose containing material. It is notable that the patent references described above do not disclose the exothermic reaction of hypochlorite salts and cellulose as a chemical heat source. In particular, none of those patent references disclose the use of cellulose as a reactant or primary reactant. Cellulose is only disclosed in three of the listed patent references, and in all three is used only as an nonreactive filler.

Hypochlorite salts are used as bleaches for laundry and as swimming pool disinfectant. As used herein, hypochlorite salts refer to the salts of hypochlorous acid. The preferred salts for use in practicing the invention are sodium hypochlorite (NaOCl) and calcium hypochlorite ($Ca(OCl)_2$), of which calcium hypochlorite is most preferred, because it is more stable for shipment and storage. Sodium hypochlorite is air-unstable, and irreversibly decomposes in hot water. Although the disclosure hereafter describes primarily calcium hypochlorite as the reactant, it will be understood that sodium hypochlorite could function in substantially the same manner, although the reaction data would differ.

Calcium hypochlorite may be used either in dry powder form, or in aqueous solution. One structure and method for combining the reactants in a convenient heat packet is to have a tough puncture and rupture resistant fluid-tight envelope, with a rupturable fluid-tight container therein. The cellulosic material, preferably dry, is placed in the envelope, around the container of calcium hypochlorite in aqueous solution. To begin the reaction, the container is ruptured, causing the hypochlorite solution to spread throughout the envelope, soaking into and reacting with the cellulosic material.

An alternate heat pack structure and reactant mixing process is to place the hypochlorite in powdered from in the packet, uniformly distributed throughout the cellulosic material. Water would be placed in a single rupturable container within the envelope, and when ruptured, would soak the cellulosic material and dissolve the calcium hypochlorite. Once the dissolved calcium hypochlorite is contacted with the cellulose of the cellulosic material, the exothermic resulting reaction generates heat.

As used herein, the term "cellulosic material" refers to any material containing cellulose, and in particular to the cellulose in particles of cotton plants. Cellulose from cotton plants is found in two conditions: (1) substantially pure cellulose in the form of lint cotton, and (2) cellulose bound up with lignin as lignocellulose.

As used herein, the term "gin trash" refers to the foreign matter, removed from seed cotton, produced as waste by a cotton gin, which may include among other material, particles of cotton plant, such as pieces of stems, leaves, bark, bolls, pith, lint fibers, and membrane, as well as dirt, pebbles, and other inorganic material. It is notable that gin trash was burned in furnaces at the gin, until environmental concerns required its disposal in other ways, such as spreading it on fields as low grade fertilizer. Gin trash is somewhat undesirable as a fertilizer, however, because of disease and weed seeds in the gin trash that are then introduces into a field on which it is spread. However, our invention enables the beneficial use of this previously wasted resource.

We prefer to use gin trash that has been processed as described in a previously filed patent application by some of the coapplicants herein, Ser. No. 676,051, filed on Nov. 29, 1984, entitled Method of Treating Cotton Burrs and other Gin Trash, resulting in the cleaned, classified and mechanically sized gin trash as described in that application. The reader is referred to the patent resulting from that application for a clear understanding of that process. Such processed gin trash has a low proportion of siliceous material therein and is preferably reduced in size to extremely small particles, e.g. that will pass through 200 to 400 mesh screen or smaller, for use in heat packets according to our invention, to expose as much lignocellulose surface to hypochlorite solution as possible.

As noted above, the lignocellulose of gin trash is essentially cellulose bound up by lignin. Although the lignin will not react with the calcium hypochlorite to an appreciable extent, the cellulose bound up with the lignin will react with the calcium hypochlorite. Therefore, it is preferred to presoak the lignocellulose particles so that the water occupies space within the porous lignocellulose particles. When the calcium hypochlorite is dissolved by the water soaked into the particles, nascent oxygen present in the aqueous hypochlorite solution will contact the cellulose, producing the desired exothermic reaction.

We have also discovered that once the initial reaction of the calcium hypochlorite and the cellulosic material, has been substantially exhausted, the addition of additional water does not promote significant further reaction or regenerate the exothermic reaction of the hypochlorite salt and cellulose. However, when additional hypochlorite salt is provided for reaction, the exothermic reaction is regenerated substantially at the same heat of reaction. We have determined that this successive reaction may be repeated many times without appreciable degradation of the reaction heat and time, until the cellulose within the lignocellulose is completely reacted.

Besides other structure that may be derived from our present disclosure, our invention facilitates the use of gin trash as a reactant. One or more rupturable, fluid-tight containers of water are within an envelope containing lignocellulose particles. Separate rupturable containers of somewhat concentrated hypochlorite solution are also spaced within the envelope. The reaction is initiated by first breaking the water filled containers, then allowing the water to soak the lignocellulose, and then to rupture one or more of the hypochlorite containers to allow the hypochlorite to mix with the soaking water and react with the cellulose.

Thus, it may be seen that the function of the total combination far exceeds the sum of the functions of the individual elements, such as envelopes, containers, and bleach, etc.

(2) Objects of this Invention

An object of this invention is the production of heat.

Further objects are to achieve the above with a device that is sturdy, compact, durable, lightweight, simple, safe, efficient, versatile, ecologically compatible, energy conserving, and reliable, yet inexpensive and easy to manufacture, transport, and use.

Other objects are to achieve the above with a method that is versatile, ecologically compatible, energy conserving, rapid, efficient, and inexpensive, and does not require skilled people to transport and use.

The specific nature of the invention, as well as other objects, uses, and advantages thereof, will clearly appear from the following description and from the accompanying drawing, the different views of which are not scale drawings.

DESCRIPTION OF THE PREFERRED EMBODIMENTS

Figure 1:
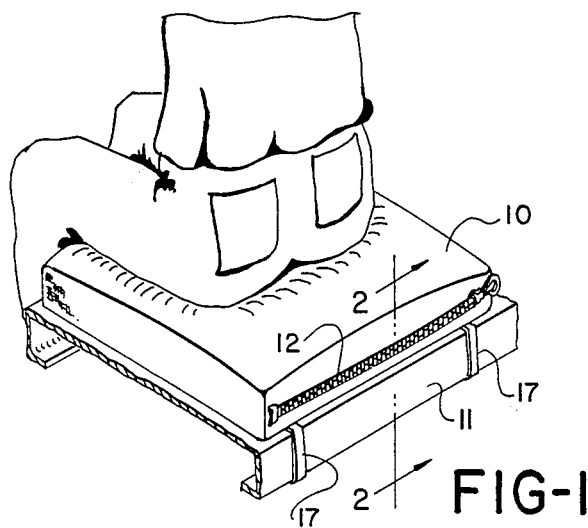
FIG. 1 shows a perspective view of a stadium seat embodiment of a chemical heater according to our invention.

As described above, our invention utilizes the thermal energy released by exothermic chemical reaction of hypochlorite salts and cellulosic materials. When in aqueous solution, hypochlorite salts form chemical complexes of nascent oxygen and chloride salts (i.e.; sodium hypochlorite (NaOCl) forms nascent oxygen (O) and sodium chloride salt (NaCl); calcium hypochlorite ($Ca(OCl)_2$) forms nascent oxygen (20) and calcium chloride salt ($CaCl_2$)).

Chlorine ($Cl_2$) will also be present in the aqueous solution ($Cl + H_2O$) when using sodium hypochlorite (NaOCl) or calcium hypochlorite ($Ca(OCl)_2$). The reaction of chlorine with water forms hypochlorous acid and hydrochloric acid (HOCl and HCl, respectively). The hypochlorous acid decomposes to form nascent oxygen and hydrochloric acid (O and HCl). Although this set of reactions produces nascent oxygen, hydrochloric acid, a strong irritant, also results.

Cellulose is a polymer of anhydroglucose units. The nascent oxygen generated by the decomposition reactions of the hypochlorite salts in aqueous solution described above oxidizes alcohol groups (OH) of the anhydroglucose units of the cellulose, resulting in the production of heat. This reaction will produce ketones or aldehydes and water. The aldehydes may be further oxidized by the nascent oxygen to form carboxylic acids, also a heat producing exothermic reaction.

The heat generated by these oxidation reactions may range from an observed 33 kcal/gmol OH, to a calculated 40 kcal/gmol OH. This heat of reaction is much less than the several hundred kcal/gmol OH produced by complete oxidation, or combination, of the cellulose. There are also several side reactions that use the nascent oxygen. Thus the reaction is unlikely to run away, or generate undesired or unexpected high heats or temperatures.

Applicants have performed many experiments using various relative combinations of water, hypochlorite salt and cellulosic material. Some of the data resulting therefrom is summarized below for illustrative purposes. The first data described below is for reactions involving substantially pure cellulose in the form of lint cotton fibers recovered from gin trash, as described above. We have observed from separate reactions of lint fibers and lignocellulose particles with aqueous hypochlorite solutions that the temperature rises at a much greater rate during the reaction with pure cellulose than with lignocellulose. This increased rate of reaction results in higher possible peak temperatures.

Tables I and II below summarize the results of many runs using varying concentrations or ratios by weight of aqueous hypochlorite solution and lint fibers retrieved from gin trash also referred to as "fiber-feed" herein. The aqueous hypochlorite solution is a 5.25 percentage concentration of calcium hypochlorite in water. The tables show the starting temperature for each different weight ratio to fiber feed (FF) of aqueous calcium hypochlorite solution used, and the temperature recorded in five minute increments.

TABLE I

| AH/FF wt ratio | Start °C. | \multicolumn{7}{c}{Temperature Profile (Heat Pack) Observed Temp (°C.) at Elapsed Time (min)} |
|---|---|---|---|---|---|---|---|---|

| AH/FF wt ratio | Start °C. | 5 | 10 | 15 | 20 | 25 | 30 | 35 |
|---|---|---|---|---|---|---|---|---|
| 2:1 | −25 | 47 | 41 | 34 | 26 | 17 | 12 | 9 |
| 6:1 | 27 | 63 | 59 | 55 | 51 | 49 | 46 | 44 |
| 6:1 | 26 | 64 | 59 | 46 | 45 | 41 | 39 | 38 |
| 4:1 | 28 | 64 | 58 | 50 | 50 | 47 | 45 | 43 |
| 2:1 | 27 | 67 | 63 | 59 | 55 | 52 | 50 | 48 |
| 1:1 | 26 | 54 | 42 | 38 | 36 | — | — | — |
| 2:1 | 26 | 63 | 61 | 59 | 57 | 53 | 51 | 49 |
| 2:1 | 27 | 62 | 54 | 54 | 52 | 50 | 47 | 46 |
| 8:1 | 26 | 65 | 61 | 58 | 56 | 54 | 51 | 50 |
| 3:1 | 26 | 60 | 49 | 42 | 40 | 38 | 37 | 35 |
| 2:1 | 27 | 57 | 50 | 46 | 42 | 40 | 38 | 36 |
| 4:1 | 27 | 60 | 56 | 52 | 48 | 46 | 45 | 44 |

TABLE II

| AH/FF wt ratio | Start °C. | 5 | 10 | 15 | 20 | 25 | 30 | 35 |
|---|---|---|---|---|---|---|---|---|
| 2:1 | 26 | 64 | 60 | 59 | 57 | 56 | 53 | 52 |
| 3:1 | 26 | 63 | 61 | 58 | 58 | 57 | 56 | 51 |
| 1:1 | 26 | 56 | 54 | 46 | 42 | 41 | 38 | 36 |
| 2:1 | 27 | 65 | 62 | 58 | 57 | 56 | 54 | 53 |
| 2:1 | 26 | 63 | 61 | 59 | 57 | 56 | 54 | 52 |
| 4:1 | 27 | 64 | 58 | 49 | 48 | 46 | 42 | 38 |
| 2:1 | 27 | 64 | 62 | 61 | 58 | 57 | 56 | 53 |
| 3:1 | 27 | 62 | 57 | 58 | 56 | 54 | 53 | 50 |
| 2:1 | 26 | 63 | 61 | 59 | 58 | 57 | 56 | 54 |
| 2:1 | 27 | 64 | 63 | 60 | 59 | 58 | 56 | 53 |
| 2:1 | 27 | 65 | 63 | 61 | 58 | 57 | 57 | 54 |
| 6:1 | 27 | 62 | 60 | 58 | 57 | 54 | 52 | 47 |

TABLE II-continued

| AH/FF wt ratio | Start °C. | 5 | 10 | 15 | 20 | 25 | 30 | 35 |
|---|---|---|---|---|---|---|---|---|
| 2:1 | 26 | 63 | 61 | 58 | 58 | 57 | 56 | 54 |

The data shown above was for the addition of varying total amounts of hypochlorite and water in aqueous solution, with the weight ratio of hypochlorite salt and water being constant at about 5.25 percent hypochlorite salt to water. We have also determined that as described above in the Summary of the Invention, the dry hypochlorite salt may also be added to soaked cellulosic material with the reaction being resumed or repeated with the addition of additional amounts of dry hypochlorite salt.

Although the data in Tables I and II above deals with the reaction of calcium hypochlorite and pure cellulose in the form of lint fibers, we have determined that the preferred form of cellulosic material is lignocellulose particles, and in particular such lignocellulose particles derived from cotton plants or being pieces of cotton plants as described above. The lignocellulose of cotton plants is particularly porous and well suited to use as a reactant. As described above, the lignocellulose particles are preferably soaked so as to allow the water to soak into the pores and into the porous spaces within the lignocellulose particles, swelling the particles, and thereby better exposing the cellulose therein to the calcium hypochlorite dissolved in the water. Because of this soaking requirement and the lesser contact initially between the cellulose and the calcium hypochlorite, the reaction of the lignocellulose particles and calcium hypochlorite solution typically progresses more slowly with a longer duration. Moreover, by varying the characteristics of the lignocellulose particles, and the relative ratios by weight of the reactants and water, various reaction times, peak temperatures, and average temperatures can be obtained.

For example, we have conducted many experiments regarding the structure and method that might be best employed in using the lignocellulose particles as a reactant in a chemical heater for personal use. We have discovered that as described above although the addition of water to an already reacted and cooled mixture of the calcium hypochlorite, water, and lignocellulose particles, that the addition of additional calcium hypochlorite, either in dry powder form or as solution, results in a regeneration of the reaction with substantially the same heat of reaction as before.

Table III shows the results of one of several experiments involving the addition of successive amounts of dry calcium hypochlorite to an initial mixture of water and gin trash. For the experiment in Table III, the heat capacity of water has been assumed to be one calorie per gram-degrees-centigrade (cal/g°C.), whereas the heat capacities of the gin trash and the calcium hypochlorite have each been assumed to be 0.5 calories per gram-degrees-centigrade (cal/g°C.).

The initial mixture of water and gin trash was 140 grams of tap water and 70.4 grams of lignocellulose particles. The temperature was monitored as the reaction was carried out in an insulated vessel to simulate adiabatic temperature rise. The data is shown in terms of grams of dry calcium hypochlorite added for each run, with the total gram amount of calcium hypochlorite added being listed in a separate column. The initial temperature upon addition of each additional amount of hypochlorite salt is shown, as well as the peak temperature rise. The heat of reaction is calculated using the assumed heat capacities noted above.

TABLE III

Heats of Reaction from Adiabatic Temperature Rise

| Run No | Ca(OCl)$_2$ Added (g) | Total (g) | Init Temp (°C.) | Temp Rise (°C.) | Heat of Reaction (cal/g) |
|---|---|---|---|---|---|
| 1 | 15.33 | 15.33 | 26 | 28 | 453 |
| 2 | 13.28 | 28.61 | 42 | 33 | 470 |
| 3 | 12.12 | 40.73 | 50 | 27 | 355 |
| 4 | 13.89 | 54.62 | 25 | 40 | 583 |
| 5 | 10.12 | 64.74 | 37 | 24 | 492 |
| 6 | 24.84 | 89.58 | 25 | 39 | 453 |

The total heat of reaction was maintained above 350 calories per gram of dry hypochlorite salt with successive temperature rises being substantially the same as, or greater than, that initially experienced in run number "1". Therefore, using the dry hypochlorite salt as a limiting reactant, the temperature rise may be spread out over a great period of time by successive additions of the hypochlorite salt. Of course, it will be understood that for convenience of addition of the hypochlorite, a somewhat concentrated hypochlorite solution could be used in place of the dry hypochlorite salt used for purposes of experiment. The utilization of these characteristics of the hypochlorite salt-gin trash reaction will be more fully illustrated hereafter.

Based upon our experiments, and the development and reduction to practice of the invention disclosed herein, we believe that the following conclusions may be made. Some of these conclusions are based on an assumed cellulose content of lignocellulose particles of about 50-60 weight percent cellulose and 40-50 percent substantially nonreactive lignin, as well as the assumptions for heat capacities described above in connection with Table III.

We believe that the potential thermal heat from reaction of hypochlorite salts and cellulosic material is about 650 calories per gram of lignocellulose particles. We also believe the minimum amount of water necessary is about 0.6 grams water for each gram of lignocellulose with the optimum amount of water being about 2 grams of water for each gram of lignocellulose. We also believe that about 2.5 grams of dry calcium hypochlorite is required to completely oxidize one gram of lignocellulose particles, assuming the particles of cotton plant are finely ground, and soaked with water. These assumptions are provided only to assist workers in the art in understanding making and using the invention disclosed herein. Of course, it will be understood that heat generation and temperature profile will depend on the various factors outlined heretofore, such as gin trash particle size, weight ratios of water, calcium hypochlorite, and lignocellulose. Of course, the system used for conducting the reaction, i.e., the type of heat packet, reaction vessel, etc., will also affect the temperature profile, since the system used will determine the heat loss experienced from the reaction mixture.

We have also determined that excess water tends to act as a heat sink. The temperature peak obtainable is reduced in proportion to the amount of water in excess of that needed for reaction.

It is anticipated that closed containers will be used, such as the heat packs, described below. Therefore, the temperature of the water during the reaction should not exceed 175° F., or about 80° C. At this temperature and above, the vapor pressure of the water begins to be excessive, so that the closed envelope, pouch, or bag used to hold the reactants will tend to expand and pressurize. In no event should the water in the packet reach boiling point, since this would generate steam, with the possibility of the envelope bursting, and hot reactants, water, and dilute hydrochloric acid being dispersed with the bursting of the bag.

Having disclosed the reaction mechanisms, some illustrative data, and some of our conclusions, some preferred practical applications of our invention for use as personal chemical heaters will now be disclosed.

Figure 2:
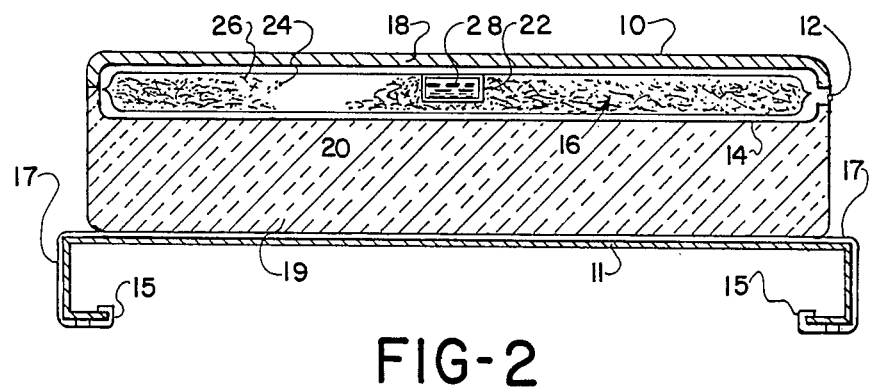
FIG. 2 shows a section view taken substantially along plane 2—2 of FIG. 1.

FIGS. 1 and 2 show a stadium seat warmer using a chemical heater according to our invention. Stadium seat cover 10 has zipper 12 in one edge thereof, which when unzipped, exposes an interior vinyl pocket 14 within the stadium seat cover for containing heat pack 16. Clips 15, connected to the cover 10 by elastic clip straps 17, secure the seat cover 10 to metal stadium bench 11. The stadium seat cover also encloses noninsulative seat padding 18, if desired, above the pocket 14, and insulation 19 below the pocket 14. The padding 18 is formed of material that will readily transmit the heat from the heat pack 16 to the seat of the user. The insulation 19 limits heat losses to the stadium bench 11.

The heat pack 16 includes envelope 20, enclosing container 22 and a mixture of gin trash 24 and lint fibers 26. The envelope 20 is preferably formed of a thin noninsulative material that is substantially puncture and rupture-proof or -resistant, such as mylar with a polyethylene inner liner, preferably extremely resistant to punctures or ruptures that would allow the contents of the envelope to escape.

The container 22 is preferably fluid-tight and rupturable, by pressure manually exerted upon the container, or by some other manual action, such as pulling of strings, tabs, and the like as well known in the heat packet art. The person using the seat warmer could simply insert the heat pack 16 in the pocket 14, zip the pocket shut, and use his or her body weight to rupture the container. Alternatively, a pull tab could be used to rupture the container, or the container could be manually ruptured by finger pressure before zipping the packet 14 shut, as desired.

The container 22, for this embodiment, contains hypochlorite solution 28, preferably aqueous calcium hypochlorite of about the same concentration as commercially available liquid laundry bleach, or about 5.25 percent by weight. There is preferably a ratio by weight of two grams hypochlorite solution for each gram of lignocellulose particles, and of about two grams of calcium hypochlorite solution for each 0.6 grams of lint fibers. The ratio of cellulose to the gin trash may be varied according to the temperature profile desired as described above.

Figure 3:
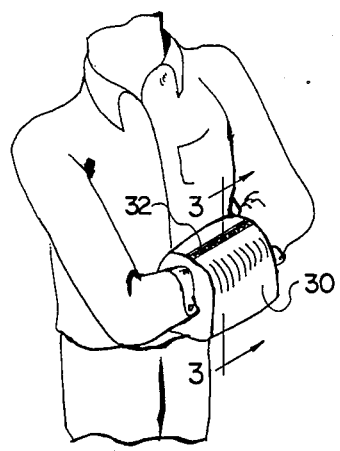
FIG. 3 shows a perspective view of a second embodiment of our invention in the form of a hand warmer.
Figure 4:
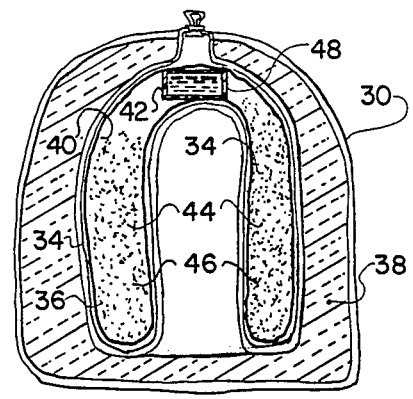
FIG. 4 shows a section taken substantially along plane 4—4 of FIG. 3.

FIGS. 3 and 4 disclose another embodiment of applicants' heat packet for use as a hand warmer. Elongated sleeve like hand warmer cover 30 encloses centrally extending sleeve 31 into which a person's hands may be inserted, as shown in FIG. 3. Zipper 32 in the cover 30 provides access to pocket 34 within the cover 30. The pocket 34 contains heat pack 36, which extends substantially around the sleeve, as shown in FIG. 4. Insulation 38 within the hand warmer cover 30, outside the pocket 34, insulates the hand warmer to prevent heat transfer to the outside air through the cover 30.

The heat pack 36 preferably includes envelope 40 which is formed of rupture and puncture resistant material, that maintains the envelope fluid tight, yet transmits heat easily, similar to the envelope material described in connection with the envelope 20 above. The envelope 40 encloses container 42, lignocellulose particles 44, and powdered anhydrous calcium hypochlorite 46. As described for the container 22 above, the container 42 is preferably liquid tight and manually rupturable. For the hand warmer shown, the packet could be inserted, the container ruptured by finger pressure, zipper 32 closed and the hands inserted into the sleeve 31.

The powdered anhydrous hypochlorite 46 is preferably uniformly mixed throughout the gin trash 44 in a ratio of about 2.5 grams of anhydrous calcium hypochlorite for each gram of lignocellulose. The container 42 contains water 48, preferably in a ratio of two grams of water for each gram of lignocellulose particles. This ratio of water to gin trash is to insure that sufficient water is present to thoroughly soak the gin trash, and provide a vehicle for dissolving the dry hypochlorite and contacting it with the cellulose within the soaked and expanded gin trash particles, as described above.

Figure 5:
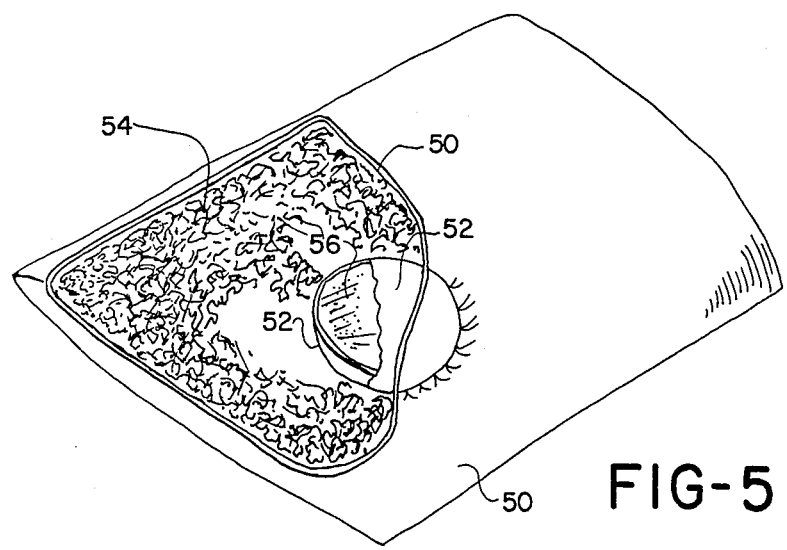
FIG. 5 shows a third embodiment of a heat pack according to our invention with parts broken away to show internal detail.

FIG. 5 discloses another embodiment of a heat pack for use in the hand warmer or stadium seat warmer, but more preferably to warm food or beverages in cans or metal containers. The heat pack includes envelope 50, enclosing container 52 and lint cotton fibers 54. The lint cotton fiber is substantially pure cellulose and therefore does not require soaking, as with the lignocellulose particles. Therefore a greater concentration of the calcium hypochlorite by weight per unit weight of water, greater than 5.25%, may be employed for this embodiment.

The envelope 50 is preferably formed of the rupture and puncture resistant material as described for the envelopes 20 and 40, except that the envelope 50 is also preferably flexible and moldable to the shape of the item to be heated.

The container 52 is preferably manually rupturable and fluid-tight as described for the containers 22 and 42 above. The container preferably contains aqueous calcium hypochlorite solution 56, which will mix thoroughly with the lint cotton fibers when the container 52 is ruptured to quickly initiate the exothermic reaction of the calcium hypochlorite and the lint cotton 54.

Figure 6:
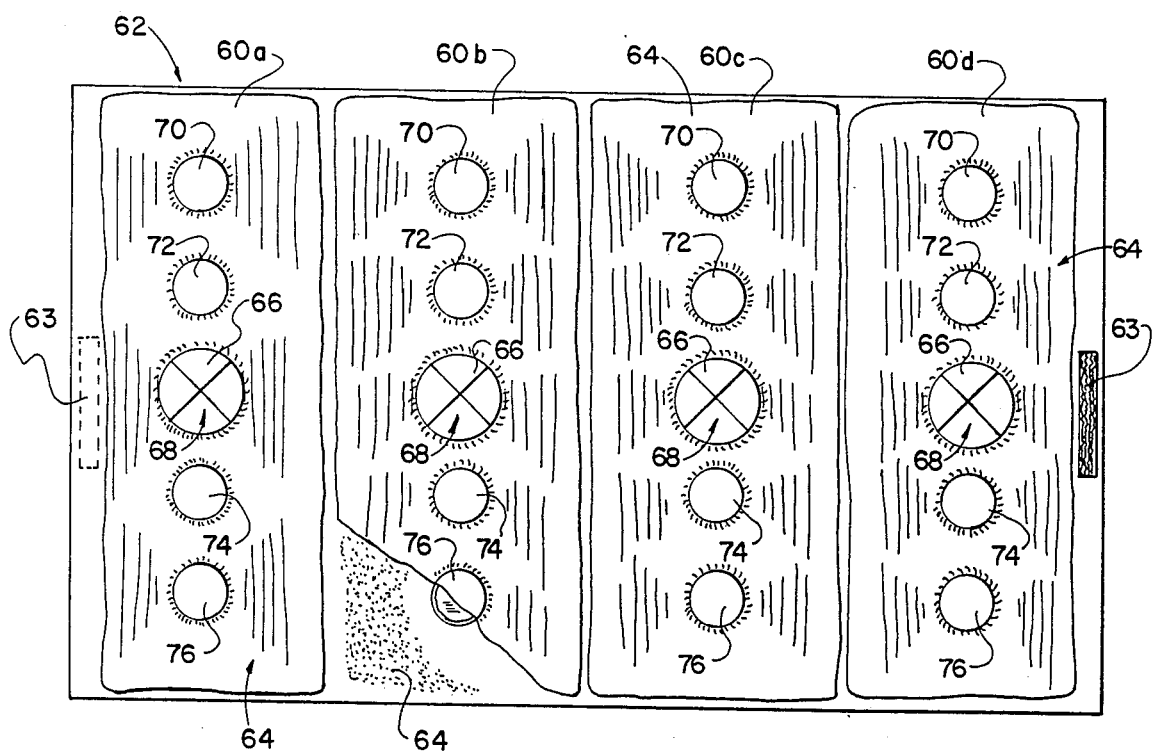
FIG. 6 shows a fourth embodiment of a heat pack according to our invention with parts broken away to shown internal detail.

FIG. 6 shows a fourth embodiment of a heat pack 62 which may be used effectively in either the hand warmer or stadium seat warmer in place of the heat packs 36 and 16, respectively, or to warm beverages or other items. The heat pack 62 as shown in FIG. 4 includes envelopes 60a, 60b, 60c, and 60d, which are each fluid-tight. The heat pack 62 preferably has "VELCRO" fasteners 63 at ends thereof to permit fastening the heat pack around cans or cylindrical containers.

Each of the envelopes 60 preferably includes lignocellulose cotton plant particles 64 and a water container 66. Each water container 66 contains sufficient water 68 to thoroughly soak the lignocellulose, preferably two grams water for each gram lignocellulose. Each of the envelopes 60 also preferably includes four hypochlorite concentrate containers 70, 72, 74, and 76. These hypochlorite containers are preferably spaced apart within each of the envelopes 60 to enable independent manual rupturing of the hypochlorite containers in any order desired.

Each of the containers 70, 72, 74, and 76 preferably contains concentrated hypochlorite solution 71, 73, 75, and 77, respectively. In designing the heat pack, the concentration by weight of the calcium hypochlorite within the solution may be varied in conjunction with varying the amount of water 68 within the water container 66. The container 66 may even be eliminated, if desired, with the water for soaking the lignocellulose particles and for contacting the calcium hypochlorite with the cellulose being provided in each of the concentrate containers, similar to the heat pack disclosed in connection with FIGS. 1 and 2. However, as described above, we have determined that it is preferable to first soak the lignocellulose to expand the particles and better expose the cellulose to the calcium hypochlorite.

This embodiment utilizes the characteristic of the hypochlorite and gin trash reaction described in connection with Table III above. The reaction started by rupturing container 70 within one envelope 60 may be allowed to reach its peak temperature and cool, whereupon container 72 could be ruptured to renew the exothermic reaction. Simultaneous rupturing of two or more hypochlorite containers adds more calcium hypochlorite, which increases the heat generated and the peak temperature.

For example, when used in the stadium seat, the multienvelope heat pack disclosed above, or a variant thereof, could be activated by rupturing the containers 70 of two envelopes, say 60a and 60c. When the seat starts to cool, such that the user desires more heat, containers 72 of the envelope 60a and 60c could be manually ruptured. Thus the heat pack embodiment shown in FIG. 6, with four envelopes 60, and four hypochlorite containers 70, 72, 74, and 76 in each envelope could provide sufficient desired heating for eight or more user selected periods.

Of course if a large reaction is desired, the containers 70, 72, 74, and 76 within one envelope 60 could be ruptured simultaneously, after the rupturing of the water container 66. Alternatively, a lesser number of the containers 70, 72, 74, and 76 could be ruptured to permit the user to customize the heat production and temperature rise of the heat pack, as desired.

Of course, for the sake of safety, as discussed above, it is desirable to limit the temperature to less than about 80° C. Thus, we prefer to design the heat pack 62 described above such that the combination of all of the water, calcium hypochlorite, and lignocellulose within the packet in any fashion will not result in temperatures in excess of 80° C.

The embodiment shown and described above is only exemplary. We do not claim to have invented all the parts, elements, or steps described. Various modifications can be made in the construction, material, arrangement, and operation, and still be within the scope of our invention.

The limits of the invention and the bounds of the patent protection are measured by and defined in the following claims. The restrictive description and drawing of the specific examples above do not point out what an infringement of this patent would be, but are to enable the reader to make and use the invention.

An an aid to correlating the terms of the claims to the exemplary drawing the following catalog of elements is provided:

CATALOG OF ELEMENTS

10: stadium seat cover

11: stadium bench
12: zipper
14: pocket
15: clips
16: heat pack
17: clip straps
18: seat padding
19: seat insulation
20: envelope
22: container
24: gin trash
26: lint cotton
28: hypochlorite solution
30: hand warmer cover
32: zipper
34: pocket
36: heat pack
38: insulation
40: envelope
42: container
44: gin trash
46: powdered dry hypochlorite
48: water
50: envelope
52: container
54: lint cotton
56: hypochlorite solution
60: envelopes
62: heat pack
63: fastener
64: gin trash
66: water container
68: water
70: containers
71: hypochlorite concentrate
72: containers
73: hypochlorite concentrate
74: containers
75: hypochlorite concentrate
76: containers
77: hypochlorite concentrate

I claim as my invention:

1. A heat pack comprising:
   a. a flexible, substantially rupture and puncture resistant, fluid-tight envelope,
   b. at least one rupturable fluid-tight container within the envelope,
   c. cellulosic material within the envelope and without the container,
   d. water within the container, and
   e. a hypochlorite salt within the envelope, with
   f. the hypochlorite salt being selected from the group consisting of sodium hypochlorite and calcium hypochlorite.

2. The invention as defined in claim 1 including the limitations a. through f. with the addition of the following limitations:
   g. said hypochlorite salt being within the container,
   h. said cellulosic material being in the form of particles of cotton plants.

3. The invention as defined in claim 1 including the limitations a. through f. with the addition of the following limitations:
   g. said hypochlorite salt being outside the container,
   h. the hypochlorite salt and the cellulosic material being substantially dry while said container is fluid-tight.

4. The invention as defined in claim 3 including the limitations a. through h. with the addition of the following limitation:
   i. said cellulosic material being in the form of particles of cotton plants.

5. The invention as defined in claim 3 including the limitations a. through h. with the addition of the following limitation:
   i. said cellulosic material including lignocellulose in the form of particles of cotton plants.

6. A heat pack comprising:
   a. a flexible, substantially rupture and puncture resistant, fluid-tight envelope,
   b. at least two rupturable, fluid-tight containers within the envelope,
   c. cellulosic material within the envelope and without the containers,
   d. water within one of the containers, and
   e. a hypochlorite salt within the other container, with
   f. the hypochlorite salt being selected from the group consisting of sodium hypochlorite and calcium hypochlorite.

7. The invention as defined in claim 6 including the limitations a. through f. with the addition of the following limitation:
   g. said cellulosic material being in the form of particles of cotton plants.

8. The invention as defined in claim 6 including the limitations a. through f. with the addition of the following limitation:
   g. said cellulosic material including lignocellulose in the form of particles of cotton plants.

9. A process for generating heat comprising the steps of:
   a. rupturing a container, containing water, within a rupture- and puncture-resistant, fluid-tight, flexible envelope,
   b. soaking cellulosic material, including particles of lignocellulose, within the envelope with the water, and
   c. swelling the lignocellulose particles with the water, then
   d. rupturing another container within the envelope, containing a hypochlorite salt, selected from the group consisting of calcium hypochlorite and sodium hypochlorite,
   e. dispersing the hypochlorite salt throughout water within the envelope,
   f. forming a hypochlorite salt aqueous solution in contact with cellulose within the swelled lignocellulose particles,
   g. oxidizing the cellulose within the swelled lignocellulose particles,
   h. transferring heat produced during said oxidizing step to outside the envelope.

10. The invention as defined in claim 9 including the limitations a. through h. with the addition of the following limitation:
    i. periodically repeating the "rupturing" step "d." through the "forming" step "f." for other hypochlorite salt solution containing containers within the envelope to reactivate said "oxidizing" and "transfering" steps "g." and "h." as desired.

11. The invention as defined in claim 9 including the limitations a. through h. with the addition of the following limitation:
    i. said lignocellulose particles being in the form of small particles of cotton plants.

* * * * *